US00PP08676P

United States Patent [19]

Yamashita et al.

[11] Patent Number: Plant 8,676

[45] Date of Patent: Apr. 5, 1994

[54] PINK DOGWOOD "BENIFUJI"

[76] Inventors: Nobuo Yamashita, 930-1, Fujimagari, Oyama-machi, Sunto-gun, Shizuoka; Hisao Ishikawa, 3451, Kamiyamakawa, Oaza, Yuki-shi, Ibaragi; Toshihiro Hagiwara, 334, Kaminoda, Oaza, Urawa-shi, Saitama, all of Japan

[21] Appl. No.: 920,618

[22] Filed: Jul. 27, 1992

[30] Foreign Application Priority Data

Aug. 1, 1991 [JP] Japan ..... 4658

[51] Int. Cl.[5] ..... A01H 5/00

[52] U.S. Cl. ..... Plt./53.2

[58] Field of Search ..... Plt. 53.2

*Primary Examiner*—James R. Feyrer

*Attorney, Agent, or Firm*—Sandler, Greenblum & Bernstein

[57] ABSTRACT

A new and distinct variety, called "Benifuji", of a pink dogwood tree substantially as herein shown and described characterized particularly as to novelty by the unique combination of the appearance of a large number of branches with an upright limb growth habit, as tall as the known variety "Miss Satomi", having leaves of medium size substantially equivalent to the wild varieties, a flower diameter of approximately 8-9 cm with the color of the flower being deep purplish pink and the distance between branches being small. The plant substantially does not become unbalanced as a result of trimming.

6 Drawing Sheets

BACKGROUND AND SUMMARY OF THE NEW PLANT

The variety "Benifuji" originated as a selection from a mass of seedlings cultured by us in our experimental nursery at Shinkyo Gotenba-shi, Sizuoka-ken, Japan. In an effort to improve the range of variation in commercial dogwood trees available in commerce, we collected seeds from wild dogwood trees of the species *Cornus kousa*, growing on the southeastern slopes of Mount Fuji. A number of seeds were collected in 1970, at an altitude ranging from about 800 to 1,000 meters above sea level. The seeds so collected were sown in mass in the above-identified experimental nursery, resulting in a large population of seedlings showing a wide range of variation in their properties and their characteristics.

The seedlings were allowed to grow. During initial screenings, seedlings having an unusually high amount of reddish coloration in the tips of the stems and leaves were screened and labeled to identify them and to distinguish them from the mass population.

In monitoring the screened and labeled plants in June 1978, an individual plant having a height of approximately 2 meters and in a very rare, red stem color with a high concentration of reddish pigment was discovered. This plant was separated from the remainder of the population, and transplanted to a different location to be further observed. This original specimen plant was observed for a period of several years and found to maintain a stable stem color, and other traits which set it apart from the remaining plants of the seedling population. At present, the original specimen of this plant has grown to a height of approximately 4.5 meters and has attained a spread of about 2.5 meters, with the trunk having a girth of 19 cm (and a diameter of approximately 6 cm, based on calculation) at a height of about 1.2 meters.

We have asexually reproduced "Benifuji" by grafting scions of "Benifuji" into seedling root stocks at our nursery at Shinkyo, Gotenba-shi, Shizuoka-ken, Japan and have found the specimens so produced to be identical to the original selection in every distinguishing characteristic.

The new variety "Benifuji" holds the following distinct characteristics:

APPEARANCE (1) A strong central leader with moderate to heavy branch density, scaffold branches strongly ascending; forming crutch angles of 45° or less with the central leader.

(2) A mature tree shape of upright to narrow upright shape, comparable to "Miss Satomi".

(3) Leaves are medium size and substantially equivalent to wild varieties.

(4) A blossom diameter of approximately 8 to 9 cm.

(5) The color of the blossom is deep purplish pink, No. 9505 in the Japanese Color Code, and No 61D or 66C in The Royal Horticultural Society Colour Chart;

(6) The distance between branches is small and tree shape can be maintained even without pruning.

GROWTH

"Benifuji" has been found to be easily asexually reproduced by grafting. Propagules started with wood from the tree may be successfully used and have been found to be reliable and are easily reproduced. The tree has been successfully and easily reproduced by grafting branches with the method of grafting and the results obtained being common to the wild *Cornus kousa* variety. Sproutlings are readily obtained around any pruned portion of the tree. The tree has been successfully asexually reproduced by rooted cuttings.

The tree appears to be as resistant as wild *Cornus kousa* to common *Cornus kousa* diseases. The tree also appears to be resistant to insect damage. To date, no severe damage by blight or insects has been observed on specimens of this plant. Additionally, this plant is relatively easy to grow.

DESCRIPTION OF THE PHOTOGRAPHS

In the accompanying photographs:

DETAILED DESCRIPTION OF THE NEW VARIETY

The following description was made with respect to plants growing at Shinkyo, Gotenba-shi, Sizuoka-ken, Japan.

Color terminology is in accordance with the ISCC-NBS method of designating colors in the United States for the literal descriptions of the colors, followed by the numerical designation for the specific color as taken from the Japan Standard Horticulture Color Chart. Selected color values are specified with reference to The Royal Horticultural Society Colour Chart where appropriate for convenient comparison.

PARENTAGE AND GROWTH HISTORY

Our plant originated as a seedling selected from a population obtained from seeds collected from native dogwood trees growing on the southeast slopes of Mt. Fuji at an altitude between about 800–1000 meters above sea level. Seed had been collected in October, 1970. Five liters of seed were originally collected. The seed were treated to break dormancy and planted in mass. In the spring of 1971, about 90% of the seeds were estimated to have germinated. The population of seedlings were repeatedly screened for seedlings having brown pigmentation in the expanding shoots, of which a number were found and identified.

From among the identified, individually screened plants, a wide range of individual characteristics were observed, including wide variations in coloration of plant parts. One individual plant, among the screened plants, was conspicuously superior in characteristics of having normal blossom character, uniform blossom distribution and an attractive, upright tree shape with strong, ascending and dense branching. Upon recognition of these superior traits, the plant of this disclosure was identified and the tree, "Benifuji", has been repeatedly multiplied asexually by grafting.

GROWTH HABIT

The claimed variety, "Benifuji", has an upright limbed growth habit with heavily branching characteristics. Branching is dense with placement of scaffold branches so close that removal of many of them will not result in loss of the tree's balanced figure.

The bark of "Benifuji" has fine texture and darker color than wild *Cornus kousa*. The color of the bark is green the first year and then changes to whitey-grey in the next year, getting darker and darker in the following years. The color eventually becomes darker than the wild *Cornus kousa* comparison variety. Texture of the bark is fine. There are no other observed differences on the bark, such as lenticels, between "Benifuji" and the wild *Cornus kousa* comparison variety.

Figure 4:
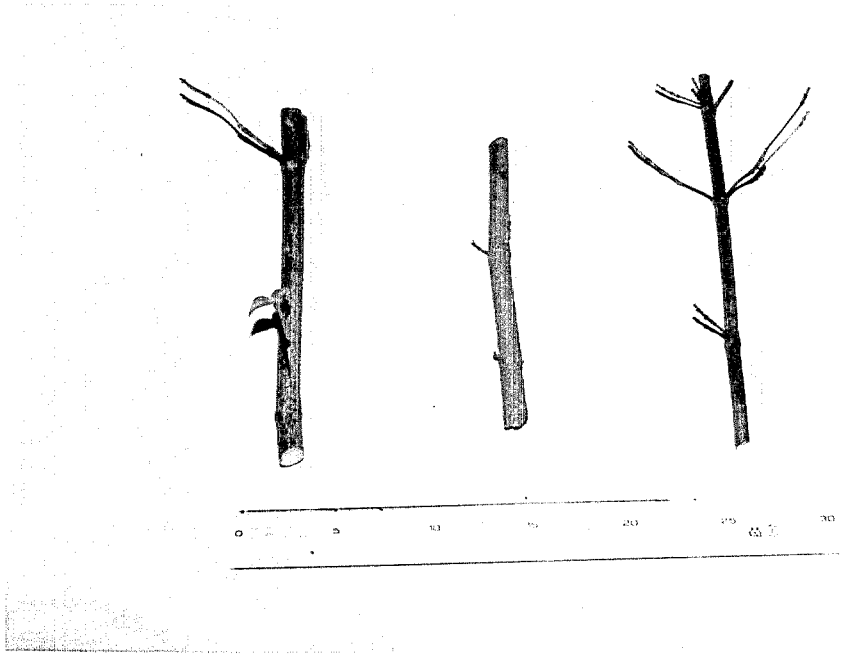
FIG. 4 shows the bark of the present variety "Benifuji" as well as a wild variety and "Miss Satomi" (right, center, left)

FIG. 4 of the drawings shows the bark of the present variety "Benifuji" as well as of a wild variety of *Cornus kousa* and "Miss Satomi" (right, center and left, respectively).

The colors of the leaves in the fall are as follows, with the colors being identified in accordance with the Japanese Color Code Nos:

Japanese Color Code Nos. 0705–0707 for "Benifuji";
Japanese Color Code Nos. 0705–0706 for both the wild *Cornus kousa* and for "Miss Satomi".

Figure 7:
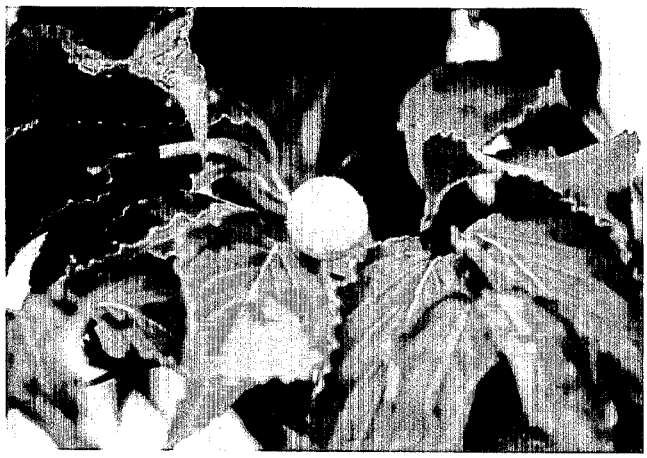
FIG. 7 shows an individual fruit of "Benifuji"
Figure 8:
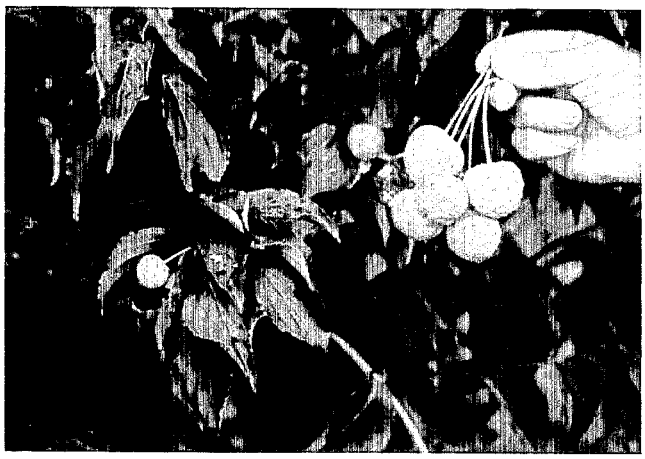
FIG. 8 shows several fruit of "Benifuji", both attached to the tree and removed therefrom.

FIGS. 7 and 8 show the fruit of "Benifuji". The multiple fruit grow up to 1.5–3.0 cm in diameter and mature in September before the fall foliage coloration.

BLOSSOMS

Figure 2:
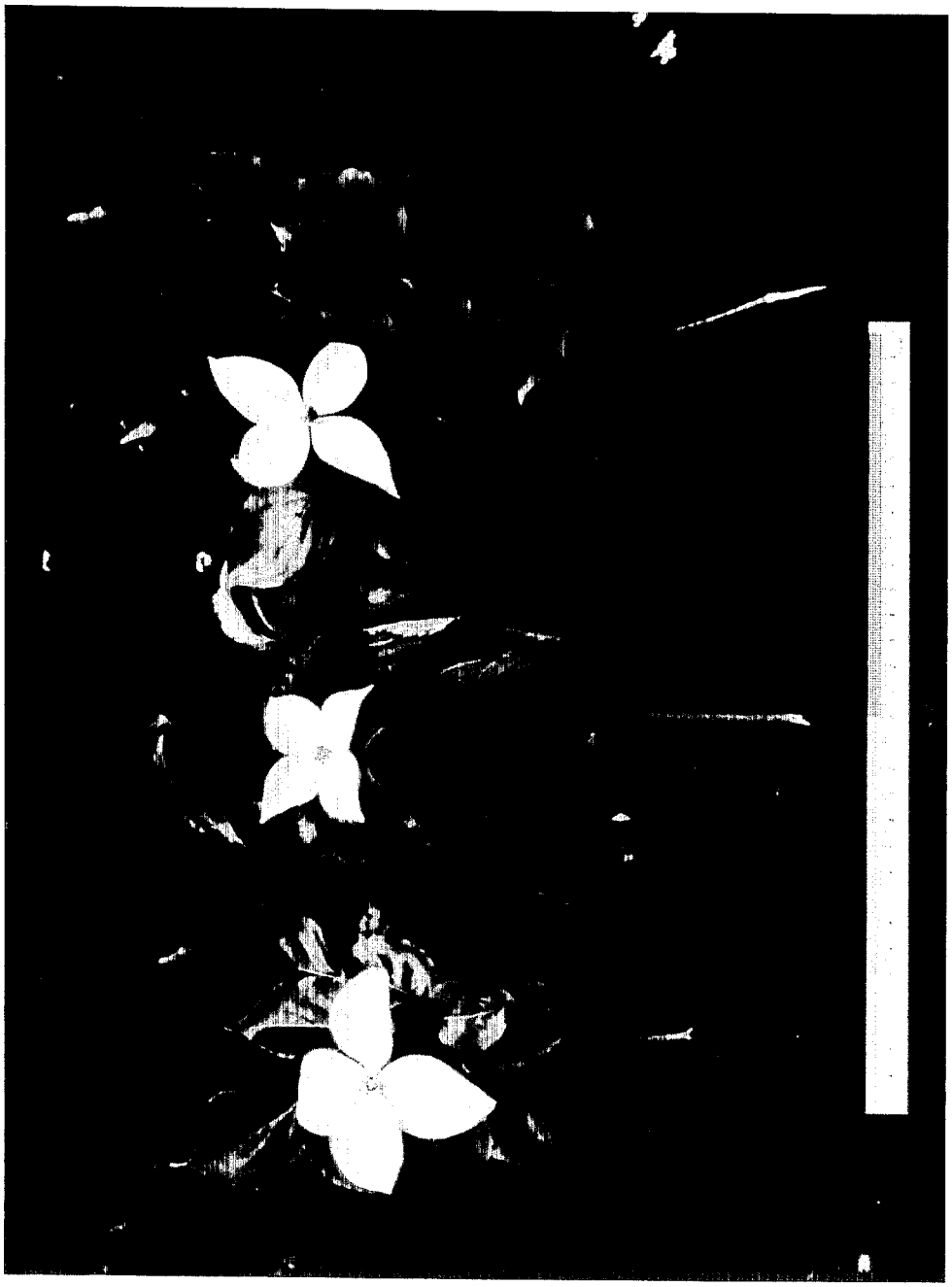
FIG. 2 shows comparison of the claimed variety, "Benifuji" and comparative varieties, i.e., the variety known as "Miss Satomi" and a wild variety.
Figure 3:
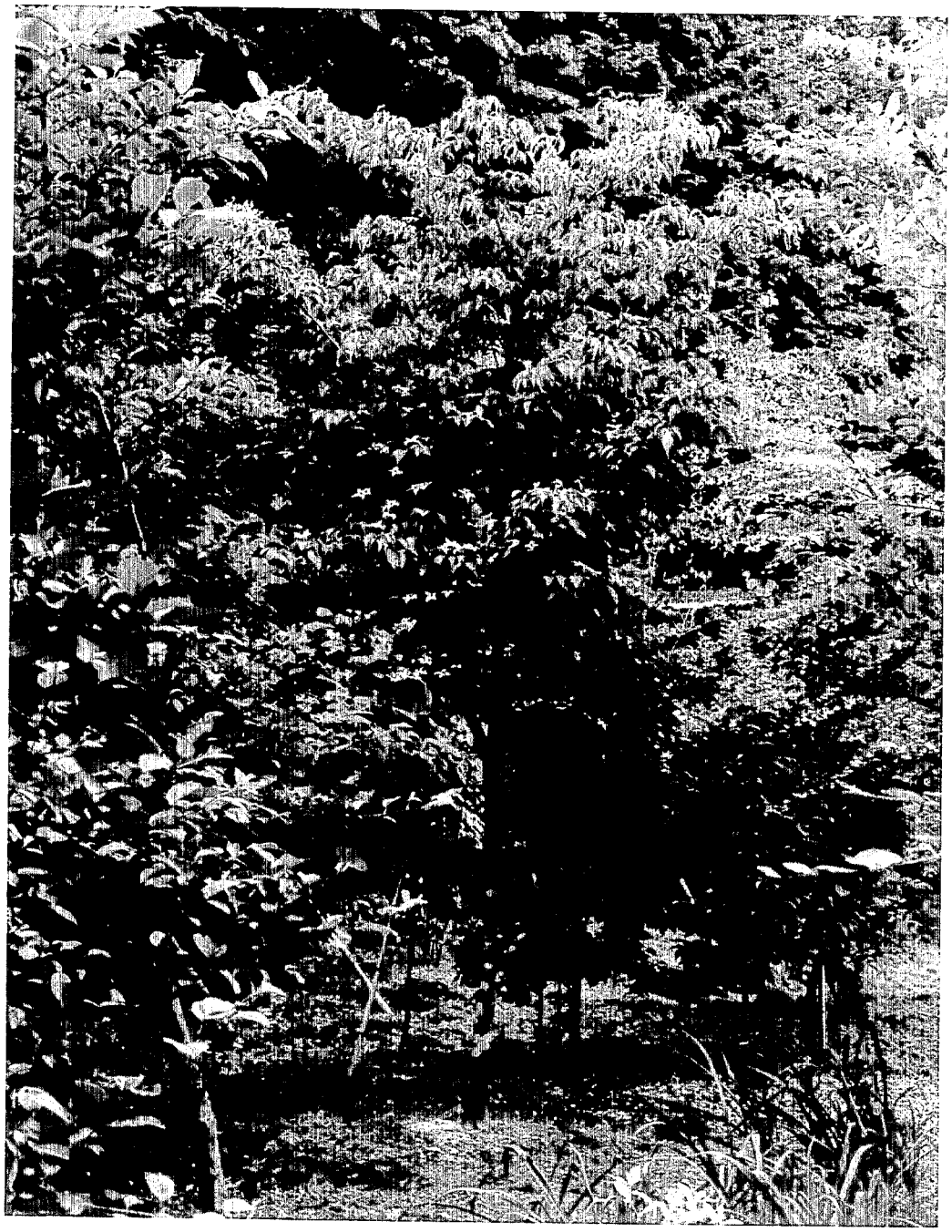
FIG. 3 shows an original specimen of the claimed variety "Benifuji", which photograph was taken on Jun. 15, 1991 at Ogawa-Machi, Sunto-gun Shizuoka-ken, Japan.

The blossoms are highly attractive and have a deep purplish pink coloration. The typical size of the blossom is approximately 8–9 cm. Blossoms are shown in FIG. 2.

TRUNK AND BRANCHES

The ramets of the tree develop into small trees having a single trunk and dominant central leader. Tree form may be obtained with minimal basal pruning. Specimens have strongly ascending branches which join the central leader in strong unions of about 45° angles. Trees are not basally dominant and form into densely branched and foliated specimens of upright figure, with tree shape being comparable to that of "Miss Satomi". A typical specimen at the above-noted production location at an age of ten years will have obtained a height of approximately 3.5 meters, a spread of approximately 2.5 meters and a trunk diameter of 4 cm at a height of 1.2 meters. After about twenty years, a typical specimen at the above-noted production location will have obtained a height of 4.5 meters.

Figure 1:
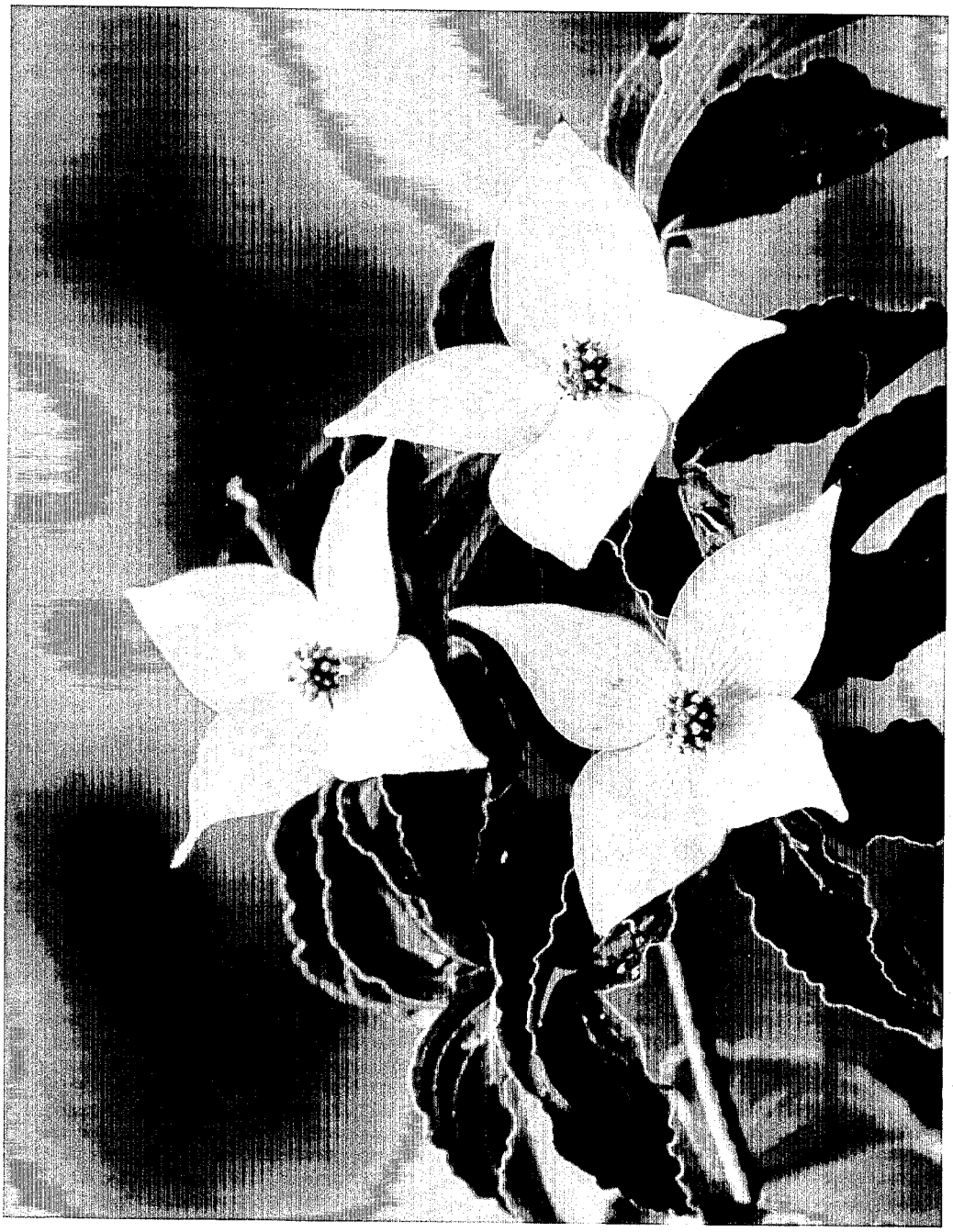
FIG. 1 shows a typical specimen of the new variety, the color of which is as nearly true as possible with the color illustrations of this character.

Limbs are strongly ascending and are densely appointed with secondary branches to form a canopy of moderate-to-heavy density, as shown in FIG. 1.

FOLIAGE

The claimed variety has leaves typically medium-sized and substantially equivalent to that of the wild dogwood which is used as a comparison example in FIG. 2.

Size: "Benifuji": 7–11 cm long (with an average of 8 cm) and 3.5–5.0 cm wide (with an average of 4.2 cm).
*Wild Cornus kousa*.—8–11 cm long, 5–6 cm wide.
*Miss Satomi*".—9–12 cm long, 7–9 cm wide.

Shape: Leaves of the claimed tree are more lanceolate and less oval than those of the comparison specimen trees.

Color: The leaves of the claimed plant are shown to be of a lighter green color than those of either comparison tree. The fall colors of the leaves are as follows, with reference to the Japanese Color Code Nos.: 0705–0707 for "Benifuji". 0705–0706 for both wild

*Cornus kousa* and "Miss Satomi". The color of the leaf stems are: Dark reddish orange (No. 0715) for Benifuji. Yellow green (No. 3511) for both wild *Cornus Kousa* and for "Miss Satomi".

The upper side margins of the leaves include a slight reddish blush but there is not any red blushed appearance nor tomentum on the underside margins of the leaves.

Characteristics of the margins: The margin of the leaves of each tree are crenate and entire; but the margin of the leaves of the claimed tree has a finely wavy character when compared with the leaves of the other two comparison trees.

Surface of the leaves: "Benifuji", wild *Cornus kousa* and "Miss Satomi" have almost equal density and attitude of tomentum, that exist only in a few delta areas (where venation and a midrib join) on the bottom surface of each leaf. The color of "Benifuji" is redder than the comparison varieties.

Glaborusness: There is no significant difference among the three varieties ("Benifuji", wild *Cornus kousa* and "Miss Satomi") in this respect.

Attitude and positioning: The leaves of "Benifuji" reflex to a much higher degree and are involute to an extent which allows for the opposite margin to nearly clasp on some leaves, while the leaves of both comparison trees are much more planar and imbricated in their positioning.

Figure 5:
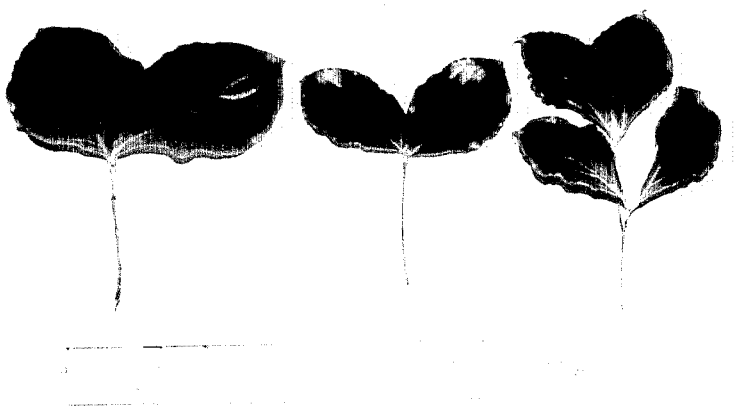
FIG. 5 shows the top surface of the leaves of "Benifuji", a wild variety and "Miss Satomi" (right, center, left)
Figure 6:
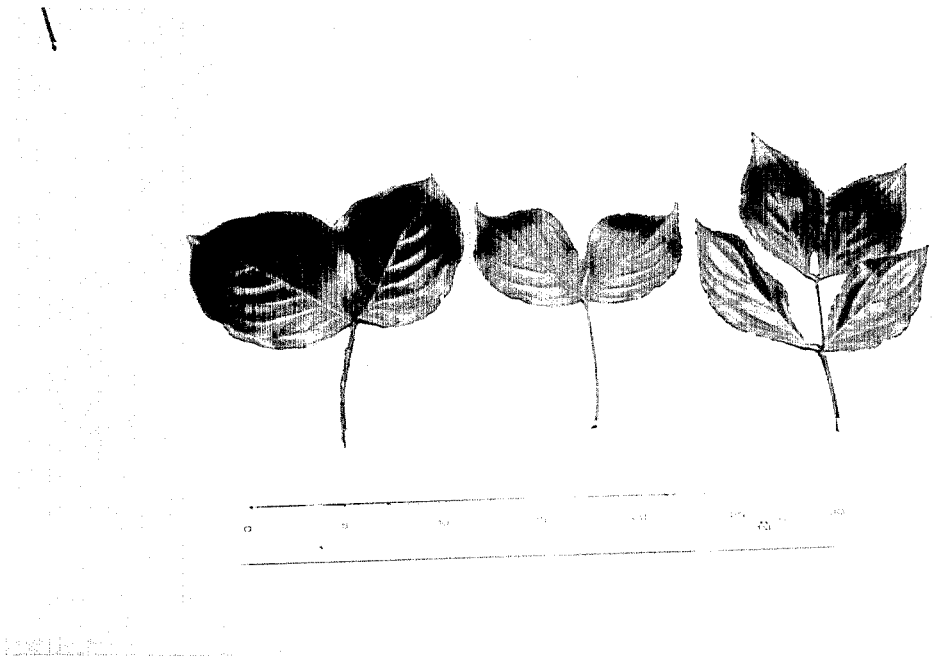
FIG. 6 shows the bottom surface of the leaves of "Benifuji", a wild variety and "Miss Satomi" (right, center, left)

Comparison of the degree of contrast between the top and bottom surfaces of the leaves can be seen most clearly with respect to FIGS. 5 and 6 of the attached photographs.

Timing of the color change: The color change occurs in the fall, wherein the leaves turn reddish. This occurs on the first and second ten days of November.

FRUIT

Fruit appears in the summer and matures in the first or second ten days of September. They are edible and taste sweet and jelly-like. Birds also eat the fruit. These traits are common to the comparison *Cornus kousa* varieties.

COMPARISON OF VARIETIES

To demonstrate the distinctiveness of the claimed variety "Benifuji", two known varieties, i.e., the variety known as "Miss Satomi" and a wild variety, which was observed in Yuki-shi Ibaragi-ken, Japan where compared.

To facilitate comparison, experimental cultivation was performed with the claimed variety "Benifuji" and with the comparative varieties, i.e., the variety known as "Miss Satomi" and the wild variety.

"Benifuji" was grafted in March of 1982 along with the variety, "Miss Satomi". A specimen of each plant was planted along with wild seedlings of *Cornus kousa* on its own stock for comparison of the growth characteristics at the above-noted culture location in the first ten days of May, 1982. The specimens were pruned only once in February, 1984 by trimming the lower branches.

On Jun. 5, 1985, blossoms and foliage, as depicted in FIG. 1, were observed on "Benifuji", but "Miss Satomi" and the wild specimen had not yet come into the flowering stage, which did not occur until, respectively, Jun. 1 and June 5, 1986, even though each specimen had received organic compound fertilizer treatment in the winter of each year. The specimens of each tree had obtained a height of about 1.5 meters by January, 1984.

In further observation of "Benifjui", the following characteristics have been observed to botanically characterize the trees:

Figure: Upright, cup-shaped.
Size: Moderately tall.
Trunk: Thin; substantially thinner than "Miss Satomi".
Branches:
- *Color.*—Grey-brown.
- *Branching.*—Densely ramose; that of "Miss Satomi" being scanty when compared to wild *Cornus kousa.* That of "Miss Satomi" can be said to be "medium" when compared to *Cornus florida.*
- *Joint span.*—Very small; that of "Miss Satomi" being wider. Join angles are about 45°.

Foliage:
- *Shape.*—Ovate elliptic; that of "Miss Satomi" being wider.
- *Tips.*—Acuminate; those of "Miss Satomi" are rounded.
- *Bases.*—Attenuate; those of "Miss Satomi" are rounded.
- *Size.*—Medium; those of "Miss Satomi" are large.
- *Character.*—Involute; those of "Miss Satomi" being flat.
- *Color.*—Strong green, R.H.S. 132B for the top surface, matt.
- *Hair.*—Present only in delta areas where venation and midribs join on the bottom surface. The hairs are fine, short and dense. They are substantially the same as "Miss Satomi" or the wild *Cornus kousa* comparison variety except for the difference in color noted above.
- *Leaf stem.*—Short green. Sunburned portions grow reddish brown. The leaf stem of the comparison trees are green.
- *Margin.*—Complete finely wavy.

Blossoms:
- *Pose.*—Upward.
- *Character.*—Single involucre of four imbricated bracts.
- *Size.*—Medium; "Miss Satomi" is of larger size.
- *Bracts.*—Ovate, thin.
- *Color.*—Deep purplish pink; R.H.S. 61D to 66C.
- *Pedicel.*—3-3.5 cm.
- *Fragrance.*—None.

Fruit:
- *Shape.*—Round.
- *Size.*—1.5 cm in diameter.
- *Seeds.*—3-5 per fruit.
- *Color.*—Moderate red orange; R.H.S. 35B, 39B, 42C, 42D, 44D, 48B, 179B, or 180B.

Foliation: Last ten days of April at the above-noted growing location.

Flowering: Over last ten days of May to middle ten days of June.

Defoliation: With the cold temperature in autumn, after the fall of frost.

Hardiness: Hardy.

Tolerates: High summer temperatures as standard for *Cornus kousa,* tolerates colder temperatures than *Cornus florida.*

Resistance: Medium resistance to disease and insects.

General: Easy to culture.

The most distinguishing characteristics of "Benifuji" might be ssen in its unusual presentation of pink or pink purplish flowers over an extended season (its blooming season coming later than *Cornus florida*), its smaller leaves of unusual shape, margin and color (the leaves of "Benifuji" having a reddish color from the beginning) for the species and its ability to develop into a densely branched and foliated specimen of moderate size and upright figure. "Benifuji" develops into mature form with a minimum of pruning, and flowers at ages earlier than comparison varieties to offer a distinctive specimen of excellent appearance in landscape use.

What is claimed is:

1. A new and distinct variety of pink dogwood plant substantially as herein shown and described, characterized particularly as to novelty by the unique combination of appearance of (1) a large number of branches and upright limb growth habit, (2) as tall as known variety "Miss Satomi", (3) medium size leaves equivalent to wild varieties, (4) a flower diameter of approximately 8–9 cm, (5) the color of the flower being deep purplish pink and (6) distance between branches is small and hardly becomes unbalanced as a result of pruning.

* * * * *